US009283170B2

(12) United States Patent
Bandyopadhyay et al.

(10) Patent No.: US 9,283,170 B2
(45) Date of Patent: Mar. 15, 2016

(54) PERSONAL CARE COMPOSITION

(75) Inventors: Punam Bandyopadhyay, Bangalore (IN); Vishi Bansal, Bangalore (IN); Vijay Ramchandra Gadgil, Bangalore (IN); Rezwan Shariff, Bangalore (IN); Ravi Kant Shukla, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 279 days.

(21) Appl. No.: 13/697,386

(22) PCT Filed: May 13, 2011

(86) PCT No.: PCT/EP2011/057790
§ 371 (c)(1),
(2), (4) Date: Feb. 4, 2013

(87) PCT Pub. No.: WO2011/144536
PCT Pub. Date: Nov. 24, 2011

(65) Prior Publication Data
US 2013/0121940 A1    May 16, 2013

(30) Foreign Application Priority Data
May 18, 2010  (IN) .................. 1559/MUM/2010

(51) Int. Cl.
A61K 8/97    (2006.01)
A61K 8/49    (2006.01)
A61Q 19/02   (2006.01)

(52) U.S. Cl.
CPC . *A61K 8/97* (2013.01); *A61K 8/498* (2013.01); *A61Q 19/02* (2013.01)

(58) Field of Classification Search
CPC .......... A61K 8/97; A61K 8/498; A61Q 19/02
USPC ......................................................... 424/62
See application file for complete search history.

(56) References Cited

U.S. PATENT DOCUMENTS

| 5,607,666 | A | 3/1997 | Masson |
| 5,670,154 | A | 9/1997 | Hara |
| 6,051,602 | A | 4/2000 | Bissett |
| 6,248,341 | B1 | 6/2001 | Anderson |
| 6,352,685 | B2 | 3/2002 | Hoshino |
| 6,455,057 | B1 | 9/2002 | Barrett |
| 6,551,602 | B1 | 4/2003 | Barrett |
| 7,314,634 | B2 | 1/2008 | Hernandez |
| 2005/0266065 | A1 | 12/2005 | Perrier |
| 2006/0018858 | A1 | 1/2006 | Chen |
| 2006/0018860 | A1 | 1/2006 | Chen |
| 2006/0018861 | A1 | 1/2006 | Chen |
| 2006/0018862 | A1 | 1/2006 | Chen |
| 2006/0165641 | A1 | 7/2006 | Pillai |
| 2007/0160550 | A1 | 7/2007 | Charles nee Newsham |
| 2007/0185038 | A1 | 8/2007 | Bissett |
| 2008/0058281 | A1 | 3/2008 | Yates |
| 2008/0095866 | A1 | 4/2008 | Declercq |
| 2008/0213198 | A1 | 9/2008 | Lintner |
| 2008/0267894 | A1 | 10/2008 | Kawaguchi |
| 2009/0004311 | A1 | 1/2009 | Uchida |
| 2009/0247490 | A1 | 10/2009 | Declercq |

FOREIGN PATENT DOCUMENTS

| CN | 101361516 | 2/2009 |
| DE | 19742025 | 3/1999 |
| DE | 102007022448 | 3/2008 |
| EP | 0919218 | 6/1999 |
| EP | 1319387 | 6/2003 |
| EP | 1840131 | 10/2007 |
| FR | 2723316 | 2/1996 |
| FR | 2806623 | 9/2001 |
| FR | 2868308 | 10/2005 |
| FR | 2926220 | 7/2009 |
| JP | 2134309 | 5/1990 |
| JP | H03275613 | 12/1991 |
| JP | 06-016531 | 1/1994 |
| JP | 6128142 | 5/1994 |
| JP | 07-061918 | 3/1995 |
| JP | 07-082133 | 3/1995 |
| JP | 7061918 | 3/1995 |
| JP | 07082133 | 3/1995 |
| JP | 07-157420 | 6/1995 |
| JP | 10101543 | 4/1998 |
| JP | 2000290124 | 10/2000 |
| JP | 2001064155 | 3/2001 |
| JP | 2007045755 | 2/2007 |

(Continued)

OTHER PUBLICATIONS

Jin Dai and Russell J. Mumper, "Plant Phenolics: Extraction, Analysis and Their Antioxidant and Anticancer Properties", Molecules 2010, 15, 7313-7352.*
Kurian et al., "Antioxidant effects of ethyl acetate extract of Desmodium gangeticum root on myocardial ishemia reperfusion injury in rat hearts", Chinese Medicine, 2010, vol. 5, No. 3, pp. 1-7.
Govindarajan et al., "High-performance liquid chromatographic method for the quantification of phenolics in 'Chyavanprash' a potent Ayurvedic drug", Journal of Pharmaceutical and Biomedical Analysis 2007, vol. 43, pp. 527-532.
Govindarajan et al., Antiinflammatory and Antioxidant Activities of Desmodium gangeticum Fractions in Carrageenan-induced Inflammed Rats, Phytotherapy Research, Jun. 29, 2007, vol. 21, No. 10, pp. 975-979.
Ingham, "The Structure of Desmocarpin, a Pterocarpan Phytoalexin from Desmodium gangeticum", Zeitschrift for Naturforschung, 1984, vol. C pp. 531-534.
Jimenez-Gonzalez et al., "Pterocarpans: interesting natural products with antifungal activity and other biological properties", Phytochem Rev, Mar. 13, 2007, vol. 7, pp. 125-154.

(Continued)

*Primary Examiner* — John Pak
*Assistant Examiner* — Nathan W Schlientz
(74) *Attorney, Agent, or Firm* — Greenberg Traurig, LLP

(57) ABSTRACT

The present invention relates to a personal care composition for topical application having a skin lightening application. It is an object of the present invention to provide for a personal care composition that comprises fractions obtained from natural sources that gives enhanced skin lightening as compared to known fractions from natural sources.

6 Claims, No Drawings

(56) References Cited

FOREIGN PATENT DOCUMENTS

| | | |
|---|---|---|
| JP | 2009120521 | 6/2009 |
| KR | 20030082765 | 10/2003 |
| WO | WO9624327 | 8/1996 |
| WO | WO0000162 | 1/2000 |
| WO | WO0119323 | 3/2001 |
| WO | WO2004006881 | 1/2004 |
| WO | WO2006020164 | 2/2006 |
| WO | WO2006117465 | 11/2006 |
| WO | WO2007128725 | 11/2007 |
| WO | WO2008034700 | 3/2008 |
| WO | WO2009052518 | 3/2009 |
| WO | WO2009122046 | 10/2009 |

OTHER PUBLICATIONS

Rathi et al., "Anti-inflammatory and anti-nociceptive activity of the water decoction Desmodium gangeticum", Journal of Ethnopharmacology, 2004, vol. 95, pp. 259-263.

Yadava et al., "A novel flavone glycoside from the stem of Desmodium gangeticum", Fitoterapia, IOB Holding Milan, 1998, vol. 69, No. 5, pp. 443-444.

PCT International Search Report in PCT application PCT/EP2011/057790 dated Oct. 7, 2011 with Written Opinion.

European Search Report in EP application EP 10 17 3854 dated Feb. 3, 2011.

IPRP in PCTEP2011057790 dated Apr. 12, 2012, pp. 1-12.

Written Opinion in EP10173854 dated Feb. 14, 2011, pp. 13-17.

\* cited by examiner

PERSONAL CARE COMPOSITION

FIELD OF THE INVENTION

The present invention relates to a personal care composition for topical application comprising selective fractions of natural materials having skin lightening applications.

BACKGROUND OF THE INVENTION

Highly pleasing skin appearance is one of the most desired expectations from personal care products from most consumers around the world. In tropical countries where consumers generally have dark skin, there is a desire to have lighter skin appearance. In consumers who live far from the tropical countries e.g. the Caucasian people who generally have lighter skin, there is a need among such consumers to have an even tanned tone of their skin. Any exposure of the skin to sunlight, in such consumers often leads to blotchy skin, referred to as freckles and in some cases they experience hyperpigmentation in localized areas of the skin. Most consumers experience blemishes on their skin after exposure to sun, on healing of wounds or after drying up of acne. In all of the above cases, consumers rely on cosmetic solutions to their skin appearance problems.

Smooth, soft and glowing skin with even skin tone and colour is thus desired by all consumers who use personal care compositions for their skin. To provide this benefit, manufacturers from around the world have tried many approaches. One very commonly used approach is to include sunscreens or sunblocks in such cosmetic products. Sunscreens or sunblocks may be organic compounds or inorganic compounds. Sunscreens or sunblocks, at the most, only maintain the basic colour of the skin and work to prevent further darkening due to exposure to radiation.

Another approach to controlling the colour, tone and appearance of the skin is the so called skin lightening approach where chemicals are added to personal care compositions which alter the formation of melanin in the skin through biochemical transformation in the stratum corneum thereby changing the colour and appearance of the skin. This approach is capable of lightening the skin beyond the basic colour of skin. While this approach has been used successfully in many cosmetic products, researchers are still struggling to improve efficacy of skin lightening agents beyond a certain threshold.

One of the drawbacks of most skin lightening actives used so far is that they are usually synthetically prepared chemical compounds. Synthetic chemicals have over time, taken a negative connotation in the consumer's mind. Hence, many consumers are more and more, preferring actives originating from or extracted from natural sources to be used in such products.

In order to provide a solution to the several drawbacks in the art listed above, the present inventors have been working for many years on deriving actives from natural sources for various personal care benefits. They found to their utter surprise that certain fractions of a specific herb *Desmodium gangeticum*, which is rich in polyphenols including high levels of flavonoids, exhibit enhanced activity in a biochemical pathway viz. tyrosinase inhibition which is indicative of improved skin lightening.

JP 7 061 918 (Tsuneo, 1995) discloses a cosmetic which contains at least one type of plant solvent extract selected from the group which is formed from *Vetiveria zizanoides, Hemidesmus indicus, Cymbopogon nardus, Piper longum, Piper chaba, Herpestris monnies, Cardiospermum halicacabum, Tinospora cordifolia, Desmodium gangeticum, Michelia champaka* and *Melaleuca leucadendron*. The benefits disclosed in this patent publication are those of antioxidant properties to enable avoiding chapped skin, and to retain the luster and springiness of the skin in a favorable manner.

JP 7 082 133 (Tsuneo, 1995) discloses a cosmetic, having a good beautifying bleaching effect, comprising a cosmetic containing at least one solvent extract selected from the group consisting of *Cymbopogen nardus, Desmodium gangeticum, Cardiospermum halicacabum, Muraya Koenigii* and *Smilax zeylanica*.

The two patent publications mentioned above have exemplified extracts of *Desmodium gangeticum* using solvents like water, ethanol and a 50% water/ethanol mixture. The present inventors have also prepared these extracts and found that they do not have the desired polyphenols and flavonoids in the claimed ranges of the present invention and therefore do not provide the desired high skin lightening benefits.

It is thus an object of the present invention to provide for a personal care composition that comprises fractions obtained from natural sources that gives enhanced skin lightening as compared to known fractions from natural sources.

SUMMARY OF THE INVENTION

According to the first aspect of the invention there is provided a skin lightening composition comprising
(a) an extract of *Desmodium gangeticum*, wherein the extract comprises more than 40% w/w polyphenols and more than 30% w/w flavonoids; and
(b) a cosmetically acceptable base.

According to a second aspect of the present invention there is provided a process for preparing an extract of *Desmodium gangeticum*, wherein the extract comprises more than 40% w/w polyphenols and more than 30% w/w flavonoids, the process comprising the steps of:
(a) heating the *Desmodium gangeticum* in water at a temperature in the range of 30 to 100° C.,
(b) separating insoluble matter to prepare an aqueous fraction;
(c) subjecting the aqueous fraction to a step of fractionating substantially water-insoluble constituents by any of the following methods
  (i) Separation using a polystyrene-based gel, for example a MCI gel;
  (ii) Separation by precipitation using mid-polar solvents selected from the group consisting of ethyl acetate, acetone, chloroform, dichloromethane, hexanes, toluene, xylene, diethyl ether, butanol, isobutyl methyl ketone and mixture therefore or
  (iii) Separation using a chemical step involving acid hydrolysis to separate out the water-insoluble constituents.

According to a third aspect of the invention there is provided a skin lightening composition comprising an extract of *Desmodium gangeticum*, wherein the extract comprises more than 40% w/w polyphenols and more than 30% w/w flavonoids, prepared according to the process of the second aspect of the invention; and a cosmetically acceptable base.

According to a fourth aspect of the invention there is provided an extract of *Desmodium gangeticum*, wherein the extract comprises more than 40% w/w polyphenols and more than 30% w/w flavonoids, for use as a skin lightening agent.

In a fifth aspect of the invention there is provided use of an extract of *Desmodium gangeticum* wherein the extract comprises more than 40% w/w polyphenols and more than 30% w/w flavonoids for the manufacture of a medicament for skin lightening.

In a sixth aspect of the invention there is provide a cosmetic method for lightening skin comprising the step of topically applying an extract of *Desmodium gangeticum* wherein the extract comprises more than 40% w/w polyphenols and more than 30% w/w flavonoids.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

"Personal Care Composition" as used herein, is meant to include a composition for topical application to skin of mammals, especially humans. Such a composition may be generally classified as leave-on or rinse off, and includes any product applied to a human body for improving appearance, cleansing, odor control or general aesthetics. The composition of the present invention can be in the form of a liquid, lotion, cream, foam, scrub, gel, soap bar or toner, or applied with an implement or via a face mask, pad or patch. Non-limiting examples of personal care compositions include leave-on skin lotions and creams, shampoos, conditioners, shower gels, toilet bars, antiperspirants, deodorants, depilatories, lipsticks, foundations, mascara, sunless tanners and sunscreen lotions. "Skin" as used herein is meant to include skin on the face and body (e.g., neck, chest, back, arms, underarms, hands, legs, buttocks and scalp).

The invention provides for a skin lightening composition comprising an extract of *Desmodium gangeticum*, the extract comprising more than 40% w/w polyphenols and more than 30% w/w flavonoids; and a cosmetically acceptable base.

*Desmodium gangeticum* (L) D C., commonly known as Shalparni (in Sanskrit) and Sarivan (in Hindi), is a small under shrub with a very short woody stem, growing throughout India mainly in tropical regions. It is well known for various medicinal formulations in Indian traditional medicine since ancient times.

The plant has been reported to contain gangetin, a pterocarpenoid which has been shown to possess anti-inflammatory and analgesic activities. *Desmodium gangeticum* has also been reported to contain alkaloids, pterocarpenoid, flavone and isoflavonoid glycosides.

As per the present invention the extract from the plant source *Desmodium gangeticum* preferably comprises more than 50% w/w polyphenols and more than 40% w/w flavonoids. The common polyphenols and flavonoids which are preferably found in the plant source for use in the composition of the invention include the compounds whose structures are given below:

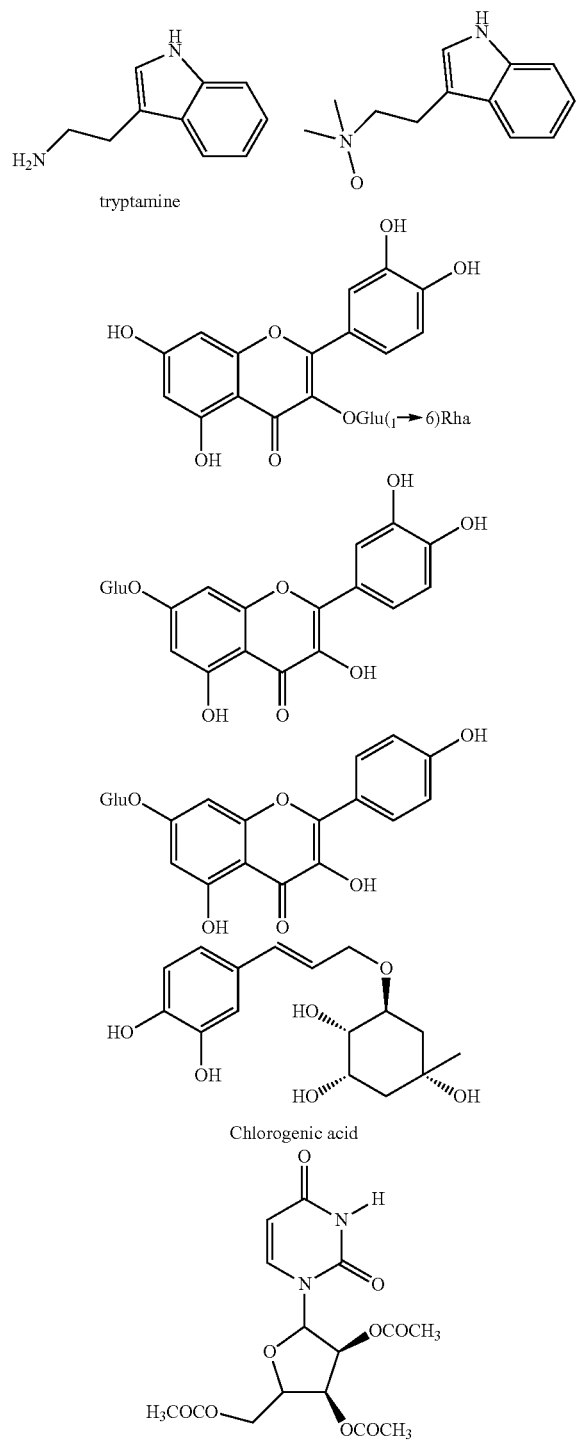

Chlorogenic acid

The extract preferably has a solubility in water in the range of 1 to 80%, more preferably 1 to 60%, further more preferably 1 to 40% w/w at 25° C. This implies that the extract from *Desmodium gangeticum* is a hydrophobic extract and therefore has low solubility in water. It has been observed that the fraction which has lower solubility in water comprises compounds like polyphenols and flavonoids in the claimed range of the present invention provide better skin lightening as evidenced by higher tyrosinase inhibition values.

The extract is preferably incorporated in 0.001 to 20%, more preferably in 0.01 to 10%, further more preferably in 0.1 to 5% w/w of the composition.

The personal care composition comprises a cosmetically acceptable base. The cosmetically acceptable base is preferably a cream, lotion, gel or emulsion.

Personal care compositions may be prepared using different cosmetically acceptable emulsifying or non-emulsifying systems and vehicles. A highly suitable base is a cream. Vanishing creams are especially preferred. Vanishing cream bases generally comprise 5 to 25% w/w fatty acid and 0.1 to 10% w/w soap. Vanishing cream base gives a highly appreciated matty feel to the skin. $C_{12}$ to $C_{20}$ fatty acids are especially preferred in vanishing cream bases, further more preferred being $C_{14}$ to $C_{18}$ fatty acids. The most preferred fatty acid is stearic acid. The fatty acid in the composition is more preferably present in an amount in the range of 5 to 20% w/w of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% w/w of the composition. Generally the vanishing cream base in cosmetic compositions is prepared by taking a desired amount of total fatty matter and mixing with potassium hydroxide in desired amounts. The soap is usually formed in-situ during the mixing. The personal care composition when formulated as a vanishing cream preferably comprises 60 to 85%, more preferably 65 to 80% w/w water.

The composition of the invention may additionally comprise another skin lightening agent other than the extract of the invention. This additional skin lightening agent is preferably chosen from a vitamin B3 compound or its derivative e.g. niacin, nicotinic acid, niacinamide or other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2,5 dihydroxybenzoic acid and its derivatives, ellagic acid, fennel extract, gluco pyranosyl-1-ascorbate, gluconic acid, glycolic acid, green tea extract, hydroquinone, 4-hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% w/w of the composition.

The personal care composition may preferably additionally comprise one or more UV sunscreens. The UV sunscreens may be inorganic or organic.

A wide variety of organic sunscreen agents are suitable for use in combination with the essential ingredients of this invention. Suitable UV-A/UV-B sunscreen agents include, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. Most suitable organic sunscreen are 2-ethylhexyl-p-methoxycinnamate and butylmethoxydibenzoylmethane.

A safe and effective amount of sunscreen may be used in the compositions of the present invention. The composition preferably comprises from about 0.1% to about 10%, more preferably from about 0.1% to about 5% w/w of a sunscreen agent.

Useful inorganic sun-blocks are also preferably used in the present invention. These include, for example, zinc oxide iron oxide, silica, such as fumed silica, and titanium dioxide.

Ultrafine titanium dioxide in either of its two forms, namely water-dispersible titanium dioxide and oil-dispersible titanium dioxide is especially suitable for the invention. Water-dispersible titanium dioxide is ultra-fine titanium dioxide, the particles of which are non-coated or which are coated with a material to impart a hydrophilic surface property to the particles. Examples of such materials include aluminium oxide and aluminium silicate. Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably 70 nm or less, more preferably from 10 to 40 nm and most preferably from 15 to 25 nm.

By topical application to the skin of a mixture of both water-dispersible ultrafine titanium dioxide and oil-dispersible ultrafine titanium dioxide, synergistically enhanced protection of the skin against the harmful effects of both UV-A and UV-B rays is achievable.

Ultrafine titanium dioxide is the preferred inorganic sun-block agent as per this invention. The total amount of sun block that is preferably incorporated in the composition according to the invention is from 0.1 to 5% w/w of the composition.

The composition according to the invention may also comprise other diluents. The diluents act as a dispersant or carrier for other materials present in the composition, so as to facilitate their distribution when the composition is applied to the skin.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate and myristyl myristate;

Solvents, such as ethyl alcohol, isopropanol, acetone, ethylene glycol monoethyl ether, diethylene glycol monobutyl ether and diethylene glycol monoethyl ether; and Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The cosmetically acceptable base is usually from 10 to 99.9%, preferably from 50 to 99% w/w of the composition, and can, in the absence of other cosmetic adjuncts, form the balance of the composition. The composition of the invention may comprise water.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition.

Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% and in many instances from 40 to 80% w/w of the composition.

Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C.

Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice are most often ethanol or sometimes iso-propanol. Polyhydric alcohols commonly comprise ethylene or propylene glycol, or a homologue can be employed such as diethylene glycol.

The compositions that remain in liquid form can be applied employing conventional applicators such as a roll-on or by being pumped or squeezed through a spray-generating orifice. Such compositions may be thickened, for example using one or more thickeners described subsequently herein.

Compositions that are firm solids, commonly obtained by use of a gellant or structurant, can be applied employing a stick applicator and soft solids, gels and creams can be applied employing an applicator having a dispensing head provided with at least one aperture through which the soft solid, gel or cream can be extruded under mild pressure.

Suitable thickeners or gellants that may be used for achieving this is by use of water-soluble or dispersible materials of higher viscosity, including various of the emulsifiers, and/or thickened or gelled with water-soluble or water-dispersible polymers including polyacrylates, and water-soluble or dispersible natural polymers, such as water-soluble polysaccharide or starch derivatives, such as alginates, carageenan, agarose and water-dispersible polymers include cellulose derivatives.

The concentration of such polymers in the water-immiscible liquid is often selected in the range of from 1 to 20% w/w depending on the extent of thickening or structuring required, and the effectiveness of the chosen polymer in the liquid/mixture.

One class of structurant which is desirable by virtue of its long standing proven capability to produce firm solids and more recently in making soft solids, comprises waxes. Herein, the term wax is employed to encompass not only materials of natural origin that are solid with a waxy feel and water-insoluble at 30-40° C., but melt at a somewhat higher temperature, typically between 50 and 95° C., such as beeswax, candelilla or carnauba wax, but also materials having similar properties. Such other waxes include hydrocarbon waxes, e.g. paraffin wax, mineral wax and microcrystalline wax; synthetic waxes, such as polyethylene of 2000 to 10000 daltons; waxy derivatives or waxy components of natural waxes Mixtures of materials within each class of gellant/structurant can be employed.

When a deodorant composition employed herein comprises an aerosol composition, it contains a propellant in addition to a base composition as described herein above, commonly in a weight ratio of from 95:5 to 40:60, and in many formulations, the weight ratio is from 90:10 to 50:50.

The propellant is conveniently a low boiling point material, typically boiling below −5° C., for example an alkane such as propane, butane or isobutane, and possibly containing a fraction of pentane or isopentane, or a hydrofluorocarbon or fluorocarbon of similar carbon content. During filling of the aerosol canister, the propellant gas is liquified by virtue of the elevated pressure that is generated therein.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

The composition is formulated in any known format, more preferred formats being creams or lotions.

Process

The present invention also provides for a process for preparing an extract of *Desmodium gangeticum*, the extract comprising more than 40% w/w polyphenols and more than 30% w/w flavonoids. The process comprises the steps of (a) heating *Desmodium gangeticum* in water at a temperature in the range of 30 to 100° C., (b) separating any insoluble matter to prepare an aqueous fraction; and (c) subjecting the aqueous fraction to a step of fractionating substantially water-insoluble constituents by any one of the following methods to prepare the extract:

(i) Separation using s polystyrene-based gel, for example a MCI gel
(ii) Separation by precipitation using mid-polar solvents selected from the group consisting of ethyl acetate, acetone, chloroform, dichloromethane, hexanes, toluene, xylene, diethyl ether, butanol, isobutyl methyl ketone and mixture therefore or (iii) Separation using a chemical step involving acid hydrolysis to separate out the water-insoluble constituents.

In a preferred aspect, the step of separation using the polystyrene-based gel, for example MCI gel, is followed by a step of solubilising said substantially water-insoluble constituents in a mid-polar solvent selected from group consisting of ethyl acetate, acetone, chloroform, dichloromethane, hexanes, toluene, xylene, diethyl ether, butanol, isobutyl methyl ketone and mixtures thereof, and then separating the solvent.

In the above step the most preferred mid-polar solvent is ethyl acetate.

Another preferred aspect of the process provides for the water-soluble fraction is dried to a powder before carrying out the rest of the process steps.

The preferred process thus involves preparing an extract which is relatively water-insoluble i.e. the extract comprises compounds which are relatively hydrophobic.

The most preferred process for preparation of the preferred extract for incorporation in the composition of the invention comprises the following steps.

(i) Extraction: *Desmodium gangeticum* is first extracted in water by heating at a temperature in the range of 30 to 100° C., more preferably in the range of 50 to 95° C. The various parts of the plant which may be used for extraction includes leaves, root or stem, preferably the aerial part or root more preferably the aerial part. The extraction is preferably carried out for 2 to 8 hours, more preferably 4 to 6 hours.

(ii) Separation of insolubles: Any insoluble matter from the extraction is then separated from the mixture. The solution containing the water extract is the aqueous fraction. This fraction is preferably dried to a powder by separating out the water preferably by evaporation, before further processing steps are carried out.

(iii) Fractionation: The aqueous fraction is then further fractionated to prepare a fraction having relatively water-insoluble constituents i.e. constituents that have water solubility in the range of 5 to 50%, more preferably from 10 to 40% w/w at 25° C. Processes that may be used to prepare this relatively water-insoluble (relatively hydrophobic) fraction are summarized below:

Separation Using MCI Gel

The separation is done through polystyrene based polymeric resin (MCI gel), e.g. one obtained from Suplco. Typical process is as follows: Solution of aqueous extract is loaded on glass column packed with MCI gel (pre-washed with ethanol or methanol and swelled in water for 2-4 h). MCI gel is a hydrophobic gel which tends to adsorb and retain hydrophobic fractions which can be further eluted with solvents of varying polarity. The process is generally done at around room temperature e.g. in the range of 20 to 30° C. The preferred mobile phase is methanol. It is preferred that the MCI gel adsorbed fraction which is separated using the MCI gel described above is further fractionated using mid-polar solvents. Preferred mid-polar solvents are ethyl acetate, acetone, chloroform, dichloromethane, hexanes, toluene, xylene, diethyl ether, butanol, isobutyl methyl ketone and mixtures thereof. The most preferred mid-polar solvent is ethyl acetate.

Separation by Precipitation Using Mid-Polar Solvents

An alternate process to prepare the desired fraction comprises the process of precipitation which involves the step of taking the powder form of the aqueous fraction and adding to a polar to mid-polar solvent at around room temperature viz. 20 to 30° C. The ratio of water-soluble fraction to solvent is preferably from 1:1 to 1:5 w/w. Preferred polar to mid-polar solvent includes methanol, ethanol, propanol, butanol and acetone. This soluble fraction may be further fractionated with mid-polar solvents like ethyl acetate, acetone, chloroform, dichloromethane, hexanes, toluene, xylene, diethyl ether, butanol and isobutyl methyl ketone. The most preferred mid-polar solvents is ethyl acetate. The desired fraction is obtained by evaporation of soluble solvent phase.

Separation Using Acid Hydrolysis

Yet another preferred process to prepare the desired fraction comprises the step of acid hydrolysis of the powder form of the aqueous fraction. Aqueous solution of extract is acidified with dilute mineral acids (e.g. hydrochloric acid or sulphuric acid) to bring pH in the range of about 2 to 5. The preferred pH is in the range of 3 to 4. The acid hydrolysis is preferably done at room temperature viz. 20 to 30° C. for about 1 to 5 hours. The precipitate obtained after acid hydrolysis is washed with water. The precipitate is the preferably dried under vacuum to obtain the desired fraction.

According to yet another aspect of the present invention there is provided use of an extract of *Desmodium gangeticum*, the extract comprising more than 40% w/w polyphenols and more than 30% w/w flavonoids, as a skin lightening agent.

The use is preferably non-therapeutic.

The invention is now further described by way of the following non-limiting examples.

EXAMPLES

Example 1

Aqueous Extract of *Desmodium gangeticum*

50 g of powdered aerial part of the herb *Desmodium gangeticum* (sourced from Arya Vastu Bhandar, Dehradun, Uttaranchal, India) was taken in a round bottom flask along with 500 ml distilled water and refluxed for 5-8 h. This was then filtered hot through muslin cloth. Filtrate was evaporated at 45° C. under reduced pressure to get a powder.

Example 2

MCI Gel Methanol Soluble Fraction of *Desmodium gangeticum*

About 10 g of the aqueous extract as prepared in example 1 was dissolved in about 200 ml of distilled water to obtain a clear solution. This solution was loaded on MCI gel resin (~50 g) packed column. The MCI gel used herein was polystyrenedivinyl-benzene resin purchased from Supelco, North Harrison Road, Bellefonte Pa., 168230048 USA. The loaded material was then eluted with water (500 ml) and methanol (500 ml). Both fractions were dried at 45° C. under reduced pressure.

Example 3

Ethanol Soluble Fraction of Aqueous Extract of *Desmodium gangeticum*

10 g of aqueous extract prepared in example 1 was taken in a round bottom flask along with 100 ml ethanol and refluxed for ~1 h. This was then filtered through whatmann filter paper. Filtrate was evaporated by using a rota evaporator at 45° C. under reduced pressure to get a powder form of the ethanol soluble fraction of aqueous extract of the herb.

Example 4

Ethyl Acetate-Soluble Sub-Fraction of Methanol Soluble Fraction of *Desmodium gangeticum*

One gram MCI gel methanol soluble fraction of example 2 was taken in a round bottom flask along with 50 ml ethyl acetate and refluxed for ~1 h. This was then filtered and evaporated at 45° C. under reduced pressure to get a powder form of the ethyl acetate soluble sub-fraction of methanol soluble fraction.

Example 5

Ethyl Acetate-Soluble Sub-Fraction of Acetone Soluble Fraction of *Desmodium gangeticum*

10 g of aqueous extract prepared in example 1 was taken in a round bottom flask along with 100 ml acetone and refluxed for ~1 h. This was then filtered and evaporated at 45° C. under reduced pressure to get a powder which is termed as acetone fraction of aqueous extract. One gram of this fraction was taken in a 100 ml round bottom flask and refluxed in ethyl acetate (50 ml). The ethyl acetate soluble part was filtered and evaporated at 45° C. under reduced pressure to get a powder which is termed as ethyl acetate soluble fraction of acetone fraction of aqueous extract.

Example 6

MCI Gel Ethyl Acetate Soluble Fraction of *Desmodium gangeticum*

About 10 g of the aqueous extract as prepared in example 1 was dissolved in about 200 ml of distilled water to obtain a clear solution. This solution was loaded on MCI gel resin (50 g) packed column. The MCI gel used herein was polystyrene-divinyl-benzene resin purchased from Supelco, North Harrison road, Bellefonte Pa., 168230048 USA. The loaded material was first eluted with ~500 ml of water and then methanol (500 ml). Methanol fraction (~1 g, dried powder) taken in a round bottom flask and stirred with ethyl acetate (~100 ml) for ~1-2 h at 45-50° C. and then filtered and evaporated at 45° C. under reduced pressure to get a powder which is termed as MCI gel ethyl acetate soluble fraction.

Solubility of the Extracts of Examples 1 to 6

The solubility of the various samples in water (at 25° C.) was measured using the following method:

10 g of the desired sample was taken in a 100 ml conical flask and 50 ml of distilled water was added to it and the mixture was stirred on a stirrer for 15 minutes at 25° C. The mixture was then filtered. The insoluble matter on the filter paper was then dried and the % insoluble matter was calculated. The filtrate was dried to a powder and weighed. The weight of the dissolved matter was then used to calculate the % solubility in water at 25° C.

Total Polyphenol and Flavonoids Content of the Extracts of Examples 1 to 6

The total polyphenol content and the flavonoids content of the various samples were measured using HPLC (flavanoids) and a colourimetic method (total poyphenol).

HPLC

Shimadzu High Performance Liquid Chromatographic system equipped with LC-10A pump with SPD-M 10Avp Photo Diode Array Detector.

Column: Phenomenex C18, 250 mm, 5 μm.
Gradient: binary

Solvent A: formic acid (0.3%) in water (mobile phase A)
Solvent B: acetonitrile (mobile phase B)
Flow rate: 0.6 ml/min.

| Time (min) | % B |
|---|---|
| 0 | 15 |
| 12 | 22 |
| 40 | 50 |
| 42 | 50 |
| 47 | 22 |
| 50 | 15 |
| 55 | stop |

Colorimetric Method

Folin Ciocalteu (FC) reagent and gallic acid as standard

Preparation of FC reagent: This is commercially available. For the assay, 20 ml of this solution was diluted to 200 ml.

Preparation of gallic acid stock solution: Gallic acid monohydrate solution was prepared by dissolving 0.110 g into a 100 ml one-mark volumetric flask with water.

Preparation of gallic acid standard solutions (A-E): Standard solutions were prepared by taking 1 to 5 ml in different flasks and diluting to 100 ml with water. These solutions are used in the assay to prepare a calibration chart.

Preparation of sodium carbonate solution: About 37.50 g of anhydrous sodium carbonate was added into a 500 ml one-mark volumetric flask. Sufficient warm water was added to half-fill the flask. This was swirled to dissolve the sodium carbonate, cooled to room temperature and diluted up to the mark with water and mixed well.

Preparation of samples: 10 mg of samples were dissolved in 10 ml of volumetric flask.

The data on the polyphenol and flavonoids content of the various samples is summarized in table 1.

The extracts from examples 1 to 6 were then evaluated for their skin lightening efficacy using mushroom tyrosinase inhibition assay, which is described below.

Mushroom Tyrosinase Assay

The assay comprised measuring O-diphenolase activities of mushroom tyrosinase with L-DOPA as substrate. This was determined spectrophotometrically by measuring the rate of dopachrome formation at 450 nm ($\epsilon=3700$ $M^{-1}cm^{-1}$). Inhibition studies were done by measuring the dopachrome formation in presence of various extracts of plant material.

The following stock solutions were prepared. 0.1 M phosphate buffer ($KH_2PO_4$, pH=6.5); 3.5 mM L-DOPA in phosphate buffer; 1 mg/ml mushroom tyrosinase enzyme (100 kU) in phosphate buffer.

To the $KH_2PO_4$ buffer (q.s. to 200 μL) in a 96 well plate having flat bottom was added the desired extract (about 6 μl) followed by 8 μL of mushroom tyrosinase enzyme. This was left at room temperature in the dark for 15 minutes to enable incubation. Then L-DOPA (57 μL, 10 mM) was added to the resultant solution and the progress of dopachrome formation was observed by measuring the absorbance at 450 nm (A450) on a TECAN spectrophotometer. Percent inhibition was calculated using (Control: without inhibitor):

% Inhibition=[(ΔA450 Control−ΔA450 Sample)/ΔA450 Control]×100.

The data on mushroom tyrosinase inhibition of the various extracts is shown in table 1. The extracts were used at ~900 ppm concentration.

TABLE 1

| Ex | Extract | Solubility in water at 25° C. | % polyphenols | % flavonoids | Efficacy (Mushroom Tyrosinase inhibition in %) |
|---|---|---|---|---|---|
| 1 | Aqueous extract | ~85-88% (±5%) | 20-26 | 16-18 | 20(±5%) |
| 2 | MCI-gel methanol soluble | ~30-35% (±5%) | 44-54 | 35-43 | 48(±5%) |
| 3 | Ethanol soluble fraction of aqueous extract | ~38-55% (±5%) | 50-60 | 42-49 | 55(±5%) |
| 4 | Ethyl acetate-soluble sub-fraction of methanol soluble fraction | ~8-18% (±5%) | 55-60 | 42-50 | 57(±5%) |
| 5 | Ethyl acetate soluble sub-fraction of acetone fraction | ~10-15% | 50-60 | 42-49 | 59(±5%) |
| 6 | MCI-gel Ethyl acetate-soluble | ~5-10% (±5%) | 65-80 | 50-65 | 70(±5%) |

The data in table 1 indicates that extracts as per the invention (examples 2 to 6) provide for vastly improved tyrosinase inhibition as compared to example outside the invention (example 1). The data also indicates that extracts as per the invention (examples 2 to 6) which give improved tyrosinase inhibition also have % polyphenols higher than 40% and % flavonoids higher than 30% as compared to example 1 where aqueous extract has significantly smaller amounts of polyphenols and flavonoids.

Examples 7 and 8

Comparison with a Positive Control

The extract of example 6, was measured at 300 ppm (example 7) for tyrosinase inhibition using human tyrosinase enzyme and the efficacy of this was compared to kojic acid at ~426 ppm ($IC_{50}$ ~3 mM) concentration (example 8). Kojic acid is known to be one of the best skin lightening agent. The data on % human tyrosinase inhibition is shown in table 2.

TABLE 2

| Ex | Extract | Efficacy (human tyrosinase inhibition in %) |
|---|---|---|
| 7 | MCI-gel Ethyl acetate-soluble | 63 |
| 8 | Kojic acid | 50 |

About $2 \times 10^4$ primary human melanocytes were seeded per well of a 96 well plate and cultures were left undisturbed for 24 hours in a 5% $CO_2$ incubator at 37° C. At 24 hours post-seeding, cultures in both plates were treated identically with different concentrations of actives (ranging from 0.01-20 ppm) or with the vehicle and left undisturbed for 72 hours. After 72 hours of incubation, one plate was used to determine viable cell counts using the Neutral Red Dye exclusion assay. The other plate was used to measure in-situ tyrosinase activity. For the latter, cultures were rinsed twice with phosphate buffer solution (PBS) (1×) and permeabilized with 40 μl of 0.5% Triton-X-100 for 1 hour on an ice bed. In-situ tyrosinase activity was visualized by addition of 60 μl of 50 mM sodium phosphate buffer (pH 6.8) containing 2 mM L-DOPA and 4 mM 3-methylbenzthaizolinone-2-hydrazone (MBTH) for 1 hour at 37° C. The reaction was stopped by the addition of 100 μl of ice-cold 10% trichloroethane (TCA) and then centrifuged at 1500 rpm for 10 minutes at 4° C. The soluble supernatant was separated from the pellet and the optical density read in a TECAN plate-reader (540 nm filter). Tyrosinase activity is expressed after correction for cell numbers (activity/NR) and represented as % control.

The data in table 2 indicates that the sample as per the invention (example 7) provides for vastly improved human tyrosinase inhibition as compared to a well known skin lightening agent such as kojic acid (example 8).

Example 10

Ethanol Extract of *Desmodium gangeticum*

10 g of powdered aerial part of *Desmodium gangeticum* (sourced from Arya Vastu Bhandar, Dehradun, Uttaranchal, India) was taken in a round bottom flask along with 300 ml ethanol and allowed to soak for five days with occasional stirring. This was then filtered through muslin cloth. Filtrate was evaporated at 45° C. under reduced pressure to get a powder form of the ethanol extract. This is a sample similar to that prepared in published document JP 7 061 918 and is outside the present invention.

Example 11

50/50 Ethanol/Water Extract of *Desmodium gangeticum*

10 g of powdered aerial part of *Desmodium gangeticum* (sourced from Arya Vastu Bhandar, Dehradun, Uttaranchal) was taken in a round bottom flask along with 150 ml of ethanol and 150 ml of water and allowed to soak for five days with occasional stirring. This was then filtered through muslin cloth. Filtrate was evaporated at 45° C. under reduced pressure to get a powder form of the 50/50 ethanol/water extract. This is a sample similar to that prepared in published document JP 7 061 918 and is outside the present invention.

The % inhibition human tyrosinase data is summarized in table 3.

TABLE 3

| Ex | Extract | Concentration (ppm) | Efficacy (human tyrosinase inhibition in %) |
|---|---|---|---|
| 9 | Extract of example 1 | 5 | 13 |
| 10 | Ethanol | 20 | 4 |

TABLE 3-continued

| Ex | Extract | Concentration (ppm) | Efficacy (human tyrosinase inhibition in %) |
|---|---|---|---|
| 11 | 50:50 Ethanol Water | 20 | 5 |
| 12 | Extract of example 6 | 5 | 28 |
| 13 | Kojic acid | 7 | 20 |

The data in table 3 indicates that sample as per the invention (example 12) provides for vastly superior tyrosinase inhibition in a human melanocyte assay as compared to samples outside the invention (examples 9 to 11). Further, the sample as per the invention (example 12) is superior to a well known skin lightening agent, kojic acid (example 13).

Example 14

Personal care composition for skin lightening in the form of a skin vanishing cream was prepared as summarized in table 4. The procedure to prepare the cream was as follows: Water phase ingredients (water, glycerine, and potassium hydroxide) were heated to 75° C. in a water-bath and molten stearic acid was added to the water phase in a Silverson mixer with stirring (at 1500 RPM) until an emulsion was formed. Remaining ingredients (except niacinamide and micronised titanium dioxide) were heated to 60° C. (oil phase) and added to the above emulsion under stirring at 2000 RPM. After 10 minutes of mixing, the emulsion was allowed to cool under constant stirring until the formation of a cream. Micronised titanium dioxide and niacinamide were added at 50° C., and perfume was added at 40° C. Extract as per example 6 was added in the oil phase.

TABLE 4

| Ingredient | Example 14 Weight % |
|---|---|
| Extract as per example 6 | 4.0 |
| Stearic acid | 13.4 |
| Potassium stearate | 5.2 |
| Glycerine | 1.0 |
| Niacinamide | 1.0 |
| Cetyl alcohol | 0.5 |
| Isopropyl myristate | 0.8 |
| Dimethicone | 0.5 |
| Micronised titanium dioxide (Tayca MT 100Z ™) | 0.2 |
| 2-ethylhexyl-4-methoxy cinnamate (Parsol MCX ™) | 0.75 |
| Butylmethoxy dibenzoylmethane (Parsol 1789 ™) | 0.4 |
| Methyl paraben | 0.2 |
| Propyl paraben | 0.1 |
| Perfume | 0.3 |
| Water | to 100 |

Example 15

Personal care composition in the form of a deo-stick for additionally providing skin lightning benefit when used on the underarm region was prepared as summarized in table 5. The procedure to prepare the stick was as follows.
Propylene glycol and PEG 200 were heated to 70-80° C. Sodium stearate powder was then added to this mixture and stirred to dissolve it. The rest of the ingredients including the extract as per example 6 were then added to prepare the final molten mixture. The mixture was then poured into tubes of desired sizes. The tubes were then refrigerated after closing the lid of the tubes for one to two hours. The deo-stick was then ejected from the tubes.

TABLE 5

| Ingredient/% by weight | Example 15 weight % |
|---|---|
| Extract as per example 6 | 2 |
| Propylene glycol | 25 |
| PEG 200 | 30 |
| Sodium stearate | 4 |
| 2-amino-2-methyl-1-propanol (AMP-95) | 0.4 |
| EDTA | 0.02 |
| BHT | 0.01 |
| Dextrin | 2.5 |
| Water | To 100 |

The present invention thus provide for a skin lightening composition that comprises fraction obtained from a natural source that gives enhanced skin lightening.

The invention claimed is:

1. A skin lightening composition comprising
   a. an extract of *Desmodium gangeticum*,
      wherein the extract comprises 65-80% w/w polyphenols and 50-65% w/w flavonoids, and the extract has a solubility in water in the range of 1 to 40% w/w of the extract at 25° C.; and
   b. a cosmetically acceptable base selected from the group consisting of a cream, a lotion, a gel and an emulsion.

2. A process for preparing an extract of *Desmodium gangeticum*, wherein the extract comprises 65-80% w/w polyphenols and 50-65% w/w flavonoids, and the extract has a solubility in water in the range of 1 to 40% w/w of the extract at 25° C., the process comprising the steps of:
   (a) heating the *Desmodium gangeticum* in water to reflux for 5 to 8 hours;
   (b) separating any insoluble matter to prepare an aqueous fraction; and
   (c) subjecting the aqueous fraction to a step of fractionating substantially water-insoluble constituents by one of the following methods:
      (i) separation using a polystyrene-based gel;
      (ii) separation by precipitation using mid-polar solvents selected from the group consisting of ethyl acetate, acetone, chloroform, dichloromethane, hexanes, toluene, xylene, diethyl ether, butanol, isobutyl methyl ketone and mixtures thereof; or
      (iii) separation using a chemical step involving acid hydrolysis to separate out the water-insoluble constituents.

3. A process as claimed in claim 2 wherein the step of separation using the polystyrene-based gel is followed by a step of solubilizing the substantially water-insoluble constituents in a mid-polar solvent selected from the group consisting of ethyl acetate, acetone, chloroform, dichloromethane, hexanes, toluene, xylene, diethyl ether, butanol, isobutyl methyl ketone and mixtures thereof, and then separating the solvent.

4. A process as claimed in claim 2 wherein the mid-polar solvent is ethyl acetate.

5. A process as claimed in claim 2 wherein the aqueous fraction is dried to a powder before carrying out the rest of the process steps.

6. A cosmetic method for lightening skin comprising the step of topically applying an extract of *Desmodium gangeticum* wherein the extract comprises 65-80% w/w polyphenols and 50-65% w/w flavonoids, and the extract has a solubility in water in the range of 1 to 40% w/w of the extract at 25° C.

* * * * *